US012597623B2

(12) United States Patent
Bataweel et al.

(10) Patent No.: US 12,597,623 B2
(45) Date of Patent: Apr. 7, 2026

(54) GENERATING POWER FROM RECYCLED HYDROCARBON GAS

(71) Applicant: Saudi Arabian Oil Company, Dhahran (SA)

(72) Inventors: Mohammed A. Bataweel, Dhahran (SA); Eyad Alali, Al Ahsa (SA); Mustafa Alkhowaildi, Safwa (SA); Nour Baqader, Khobar (SA); Norah Aljuryyed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 695 days.

(21) Appl. No.: 17/944,919

(22) Filed: Sep. 14, 2022

(65) Prior Publication Data

US 2024/0088419 A1     Mar. 14, 2024

(51) Int. Cl.
| | |
|---|---|
| *H01M 8/0606* | (2016.01) |
| *C01B 3/042* | (2026.01) |
| *C01B 5/00* | (2006.01) |
| *C01B 17/04* | (2006.01) |
| *C12P 3/00* | (2006.01) |
| *E21B 41/00* | (2006.01) |

(Continued)

(52) U.S. Cl.
CPC ........... *H01M 8/0606* (2013.01); *C01B 3/042* (2013.01); *C01B 5/00* (2013.01); *C01B 17/0426* (2013.01); *C01B 17/0495* (2013.01); *C12P 3/00* (2013.01); *E21B 41/0085* (2013.01); *H01M 8/0656* (2013.01); *H01M 10/44* (2013.01); *H01M 10/46* (2013.01);

*H01M 16/006* (2013.01); *H02J 7/342* (2020.01); *H02J 15/008* (2020.01); *H01M 2220/10* (2013.01); *H01M 2250/10* (2013.01)

(58) Field of Classification Search
CPC ... H01M 8/0606; H01M 8/0656; H01M 10/44
See application file for complete search history.

(56) References Cited

U.S. PATENT DOCUMENTS

| | | |
|---|---|---|
| 5,202,194 A | 4/1993 | VanBerg, Jr. |
| 9,397,361 B2 | 7/2016 | Papile |

(Continued)

FOREIGN PATENT DOCUMENTS

WO      WO 2016167835      10/2016

OTHER PUBLICATIONS

Ghahraloud et al., "Hydrogen Production through Thermal Decomposition of Hydrogen Sulfide: Modification of the Sulfur Recovery Unit to Produce Ultrapure Hydrogen," Industrial & Engineering Chemistry Research, Sep. 2018, 57(42):14114-14123, 10 pages.

(Continued)

*Primary Examiner* — Olatunji A Godo
(74) *Attorney, Agent, or Firm* — Fish & Richardson P.C.

(57)     ABSTRACT

Techniques for generating electric power for well site operations include processing a hydrocarbon fluid produced from a subterranean formation, through a wellbore, and to a terranean surface into at least one acid gas; processing the at least one acid gas into hydrogen; generating, with the hydrogen, electrical power from a hydrogen engine; and providing the generated electrical power for use or storage to power at least one electrically-operated machine to perform at least one well site operation.

26 Claims, 4 Drawing Sheets

(51) Int. Cl.

| | |
|---|---|
| *H01M 8/0656* | (2016.01) |
| *H01M 10/44* | (2006.01) |
| *H01M 10/46* | (2006.01) |
| *H01M 16/00* | (2006.01) |
| *H02J 7/34* | (2006.01) |
| *H02J 15/00* | (2006.01) |

(56) References Cited

U.S. PATENT DOCUMENTS

| | | | |
|---|---|---|---|
| 11,167,242 B1 | 11/2021 | Parker et al. | |
| 2013/0323614 A1 | 12/2013 | Chapman et al. | |
| 2015/0377079 A1* | 12/2015 | Noureldin | C10K 1/046 |
| | | | 60/671 |
| 2022/0127933 A1* | 4/2022 | Snoswell | B60L 53/80 |

OTHER PUBLICATIONS

International Search Report and Written Opinion in International Appln. No. PCT/US2023/032466, mailed on Dec. 8, 2023, 16 pages.

Ni et al., "Potential of renewable hydrogen production for energy supply in Hong Kong," International Journal of Hydrogen Energy, Aug. 2006, 31(10):1401-1412, 12 pages.

De Crisci et al., "Hydrogen from hydrogen sulfide: towards a more sustainable hydrogen economy," International Journal of Hydrogen Energy, 2018, 29 pages.

DeLude Consulting Inc., "Hydrogen from Hydrogen Sulphide Technology Scan and Evaluation," Prepared for Cosia, Jun. 2017, 47 pages.

Gregory et al., "Electrolysis of liquid hydrogen sulphide," Journal of Applied Electrochemistry, May 1980, 10:405-408, 4 pages.

Hajar et al., "Sulfur as a Fuel Source in a Combined Power Cycle Equipped with a Dry Flue Gas Desulfurization System," Energy Fuels, 2016, 30(10):8511-8519, 9 pages.

Palma et al., "Catalytic oxidative decomposition of H2S for hydrogen production," Chemical Engineering Transactions, Aug. 2018, 70:325-330, 7 pages.

Startsev, "The Reaction Mechanisms of H2S Decomposition into Hydrogen and Sulfur: Application of Classical and Biological Thermodynamics," Journal of Thermodynamics & Catalysis, May 2017, 8(2):1000186, 8 pages.

Stefanakos et al., "Hydrogen Production from Hydrogen Sulfide in IGCC Power Plants," Technical Report, Oct. 2007, 20 pages.

* cited by examiner

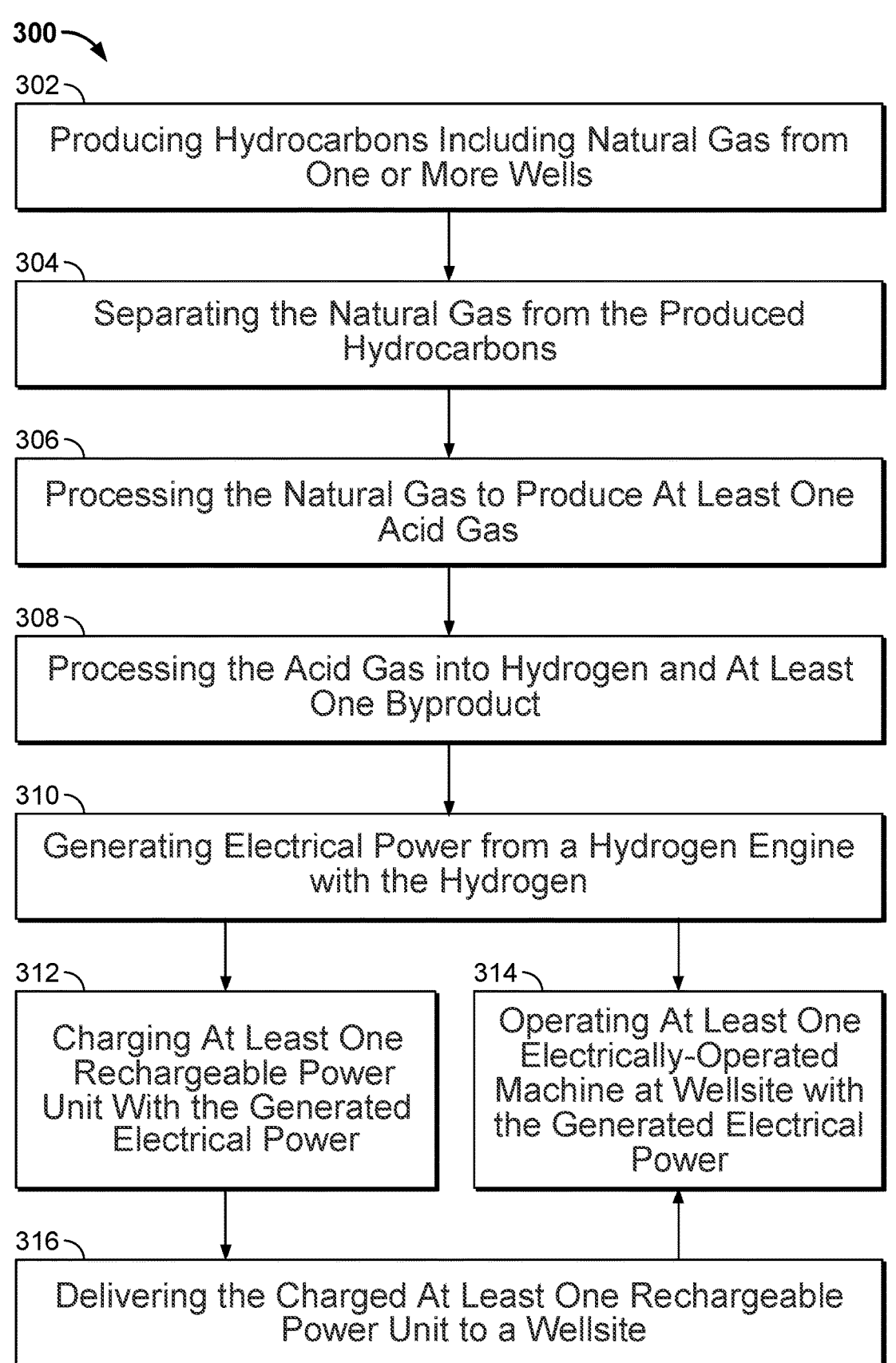

300

302 — Producing Hydrocarbons Including Natural Gas from One or More Wells

304 — Separating the Natural Gas from the Produced Hydrocarbons

306 — Processing the Natural Gas to Produce At Least One Acid Gas

308 — Processing the Acid Gas into Hydrogen and At Least One Byproduct

310 — Generating Electrical Power from a Hydrogen Engine with the Hydrogen

312 — Charging At Least One Rechargeable Power Unit With the Generated Electrical Power 314 — Operating At Least One Electrically-Operated Machine at Wellsite with the Generated Electrical Power 316 — Delivering the Charged At Least One Rechargeable Power Unit to a Wellsite

FIG. 3

GENERATING POWER FROM RECYCLED HYDROCARBON GAS

TECHNICAL FIELD

The present disclosure describes systems and methods for generating power, such as electrical power, from recycled hydrocarbon gas, such as hydrogen sulfide.

BACKGROUND

Hydrocarbon recovery operations, from drilling to secondary completion and recovery operations such as hydraulic fracturing, often require power. Conventionally, such power is supplied by diesel engines that are located at a well site. This can be expensive and cumbersome. Furthermore, hydrocarbon production often results in the recovery of harmful fluids, such as acid gasses, that need to be processed or disposed of.

SUMMARY

In an example implementation, a method of generating electric power for well site operations includes processing a hydrocarbon fluid produced from a subterranean formation, through a wellbore, and to a terranean surface into at least one acid gas; processing the at least one acid gas into hydrogen; generating, with the hydrogen, electrical power from a hydrogen engine; and providing the generated electrical power for use or storage to power at least one electrically-operated machine to perform at least one well site operation.

In an aspect combinable with the example implementation, the at least one acid gas includes hydrogen sulfide.

In another aspect combinable with any of the previous aspects, processing the at least one acid gas into the hydrogen includes converting the hydrogen sulfide into the hydrogen through a Claus reaction, including processing the hydrogen sulfide and oxygen into water and sulfur dioxide; processing the sulfur dioxide and the hydrogen sulfide into sulfur and water; and processing the water into the hydrogen and oxygen.

In another aspect combinable with any of the previous aspects, processing the at least one acid gas into the hydrogen includes converting the hydrogen sulfide into the hydrogen through an electrolytic reaction, including processing the hydrogen sulfide and at least two electrons to produce sulfur at an anode of an electrolysis cell of the electrolytic reaction and the hydrogen at a cathode of the electrolysis cell.

In another aspect combinable with any of the previous aspects, processing the at least one acid gas into the hydrogen includes converting the hydrogen sulfide into the hydrogen through a thermal decomposition reaction, including dissociating, with heat from an external heat source or a microwave source, the hydrogen sulfide into the hydrogen and sulfur.

Another aspect combinable with any of the previous aspects further includes enhancing the dissociation with a catalyst.

In another aspect combinable with any of the previous aspects, processing the at least one acid gas into the hydrogen includes converting the hydrogen sulfide into the hydrogen through a biological reaction, including introducing one or more microorganisms to the hydrogen sulfide; and producing the hydrogen and sulfur from the hydrogen sulfide through one or more biological processes performed with the one or more microorganisms.

In another aspect combinable with any of the previous aspects, generating, with the hydrogen, electrical power from the hydrogen engine includes introducing the hydrogen and atmospheric air into at least one fuel cell of the hydrogen engine; converting the hydrogen into positively and negatively charged hydrogen ions in the at least one fuel cell; flowing the positively charged hydrogen ions from an anode of the at least one fuel cell to a cathode of the at least one fuel cell to generate an electrical current to produce the electrical power; and producing water from the at least one fuel cell by combining the negatively charged hydrogen ions with the atmospheric air.

In another aspect combinable with any of the previous aspects, providing the generated electrical power for use or storage includes electrically connecting at least one rechargeable battery to the at least one fuel cell; and electrically charging the at least one rechargeable battery with the produced electrical power from the at least one fuel cell.

Another aspect combinable with any of the previous aspects further includes, subsequent to electrically charging the at least one rechargeable battery with the produced electrical power from the at least one fuel cell: delivering the charged at least one rechargeable battery to a well site; electrically connecting the charged at least one rechargeable battery to an electrically-operated machine at the well site; and operating the electrically-operated machine at the well site to perform the well site operation with the charged at least one rechargeable battery.

In another aspect combinable with any of the previous aspects, providing the generated electrical power for use or storage includes directly connecting the at least one fuel cell to the at least one electrically-operated machine at a well site; and operating the electrically-operated machine at the well site to perform the well site operation with the produced electrical power.

In another aspect combinable with any of the previous aspects, the electrically-operated machine includes at least one of a hydraulic fracturing pump, a hydraulic fracturing blender, a logging machine, a wireline machine, an electrical submersible pump, a sub-surface fluid pump, or a sand system.

In another example implementation, an electric power generation system for well site operations includes a hydrocarbon processing sub-assembly configured to process a hydrocarbon fluid produced from a subterranean formation, through a wellbore, and to a terranean surface into at least one acid gas; an acid gas processing sub-assembly configured to receive the at least one acid gas from the hydrocarbon processing sub-assembly and process the at least one acid gas into hydrogen; at least one hydrogen engine configured to generate electrical power from the hydrogen processed by the acid gas processing sub-assembly; and at least one power storage unit configured to electrically couple to the at least one hydrogen engine to receive and store the generated electrical power.

In an aspect combinable with the example implementation, the at least one acid gas includes hydrogen sulfide.

In another aspect combinable with any of the previous aspects, the acid gas processing sub-assembly is configured to convert the hydrogen sulfide into the hydrogen through a Claus reaction by performing operations including processing the hydrogen sulfide and oxygen into water and sulfur dioxide; processing the sulfur dioxide and the hydrogen sulfide into sulfur and water; and processing the water into the hydrogen and oxygen.

In another aspect combinable with any of the previous aspects, the acid gas processing sub-assembly is configured to convert the hydrogen sulfide into the hydrogen through an electrolytic reaction by performing operations including processing the hydrogen sulfide and at least two electrons to produce sulfur at an anode of an electrolysis cell of the electrolytic reaction and the hydrogen at a cathode of the electrolysis cell.

In another aspect combinable with any of the previous aspects, the acid gas processing sub-assembly is configured to convert the hydrogen sulfide into the hydrogen through a thermal decomposition reaction by performing operations including dissociating, with heat from an external heat source or a microwave source, the hydrogen sulfide into the hydrogen and sulfur.

In another aspect combinable with any of the previous aspects, the acid gas processing sub-assembly is configured to convert the hydrogen sulfide into the hydrogen through the thermal decomposition reaction by enhancing the dissociation with a catalyst.

In another aspect combinable with any of the previous aspects, the acid gas processing sub-assembly is configured to convert the hydrogen sulfide into the hydrogen through a biological reaction by performing operations including introducing one or more microorganisms to the hydrogen sulfide; and producing the hydrogen and sulfur from the hydrogen sulfide through one or more biological processes performed with the one or more microorganisms.

In another aspect combinable with any of the previous aspects, the at least one hydrogen engine includes at least one fuel cell.

In another aspect combinable with any of the previous aspects, the at least one hydrogen engine is configured to generate electrical power from the hydrogen processed by the acid gas processing sub-assembly by performing operations including introducing the hydrogen and atmospheric air into the at least one fuel cell; converting the hydrogen into positively and negatively charged hydrogen ions in the at least one fuel cell; flowing the positively charged hydrogen ions from an anode of the at least one fuel cell to a cathode of the at least one fuel cell to generate an electrical current to produce the electrical power; and producing water from the at least one fuel cell by combining the negatively charged hydrogen ions with the atmospheric air.

In another aspect combinable with any of the previous aspects, the at least one power storage unit includes at least one rechargeable battery electrically connected to the at least one fuel cell, and the at least one fuel cell is configured to electrically charge the at least one rechargeable battery with the produced electrical power from the at least one fuel cell.

In another aspect combinable with any of the previous aspects, the at least one rechargeable battery is configured to electrically connect to an electrically-operated machine at a well site to operate the electrically-operated machine at the well site to perform a well site operation with the charged at least one rechargeable battery.

In another aspect combinable with any of the previous aspects, the at least one fuel cell is configured to electrically connect to an electrically-operated machine at a well site to operate the electrically-operated machine at the well site to perform a well site operation with the produced electrical power.

In another aspect combinable with any of the previous aspects, the electrically-operated machine includes at least one of a hydraulic fracturing pump, a hydraulic fracturing blender, a logging machine, a wireline machine, an electrical submersible pump, a sub-surface fluid pump, or a sand system.

In another example implementation, an electric power generation system for well site operations includes a hydrocarbon processing sub-assembly configured to process a hydrocarbon fluid produced from a subterranean formation, through a wellbore, and to a terranean surface into hydrogen sulfide; means for processing the hydrogen sulfide into hydrogen; at least one hydrogen fuel cell configured to generate electrical power from the hydrogen; and at least one rechargeable battery configured to electrically couple to the at least one hydrogen fuel cell to receive and store the generated electrical power.

In an aspect combinable with the example implementation, the means for processing includes at least one of: means for processing the hydrogen sulfide into hydrogen through a Claus reaction; means for processing the hydrogen sulfide into hydrogen through a thermal decomposition reaction; means for processing the hydrogen sulfide into hydrogen through a biological reaction; or means for processing the hydrogen sulfide into hydrogen through an electrolytic reaction.

In another aspect combinable with any of the previous aspects, the means for processing the hydrogen sulfide into hydrogen includes means for processing the hydrogen sulfide into sulfur.

In another aspect combinable with any of the previous aspects, the sulfur is usable to generate additional electrical power with an outlet gas desulfurization unit through a desulfurization reaction.

Implementations of systems and methods for generating electrical power for a well site operation can include one, some, or all of the following features. For example, implementations according to the present disclosure can process harmful acid gasses, such as hydrogen sulfide, into other gasses, such as hydrogen and sulfur, that can be used to generate power. As another example, implementations according to the present disclosure can provide for mobile electrical power in rechargeable batteries that can be used at remote well sites. As another example, implementations according to the present disclosure can be used to promote clean energy and support sustainability. As another example, systems and methods for generating electrical power for a well site operation according to the present disclosure can be implemented at an oil and gas processing plant (in other words, a hydrocarbon processing plant) and, in some aspects, apart from a remote charging site based on recycling an acid gas for plant operations. As another example, systems and methods for generating electrical power for a well site operation according to the present disclosure can implement a battery charging site using recycling acid gas can be built on a selected remote well site and the recharged batteries can be transported from this site other remote operations nearby. Further, systems and methods for generating electrical power for a well site operation according to the present disclosure can increase a feasibility and profitability of producing wells with high acid gas concentrations by turning such acid gasses (which can be dangerous and costly to produce) into a highly demanded product: energy.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIG. 3 is a flowchart that describes an example method of generating electrical power according to the present disclosure.

DETAILED DESCRIPTION

Figure 1:
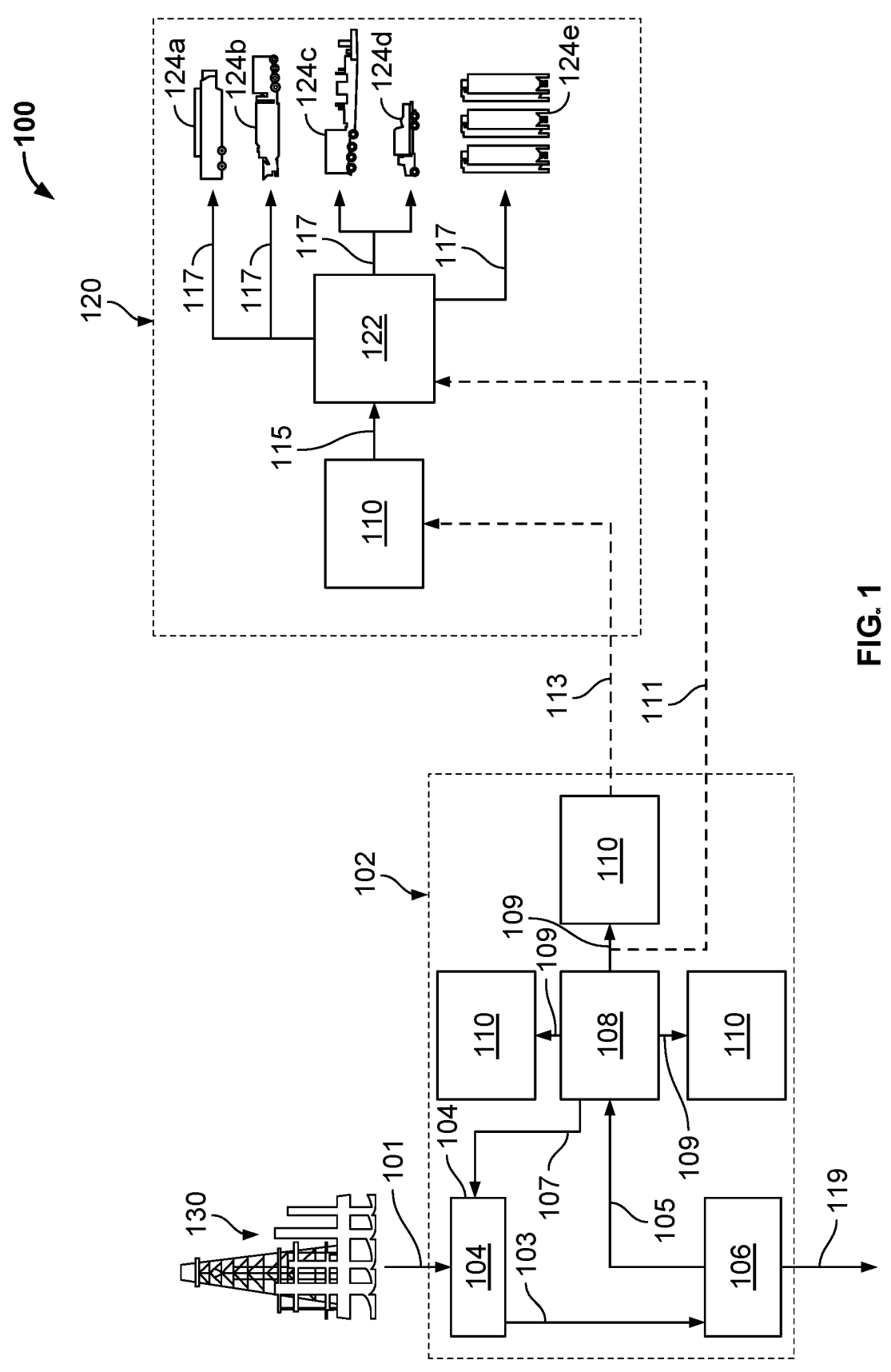
FIG. 1 is a schematic illustration of a power generation system that uses a recycled hydrocarbon gas, such as an acid gas, to generate electrical power for a well site operation according to the present disclosure.

FIG. 1 is a schematic illustration of a power generation system 100 ("system 100") that uses a recycled hydrocarbon gas, such as an acid gas, to generate electrical power for a well site operation according to the present disclosure. In example implementations, the system 100 operates to generate an amount (for example, a flow or fixed volume) of hydrogen from a hydrocarbon fluid produced from one or more wells as a source of energy for power generation. In some aspects, an acid gas, such as hydrogen sulfide (H2S) can be processed from a hydrocarbon fluid, such as natural gas, to produce the hydrogen (in other words, H2). Often processing the acid gas can eliminate a harmful gas and convert it into the hydrogen as well as a byproduct (for example, sulfur). The hydrogen can be used for power generation to support, for example, electrical power needs of the system 100, as well as to be stored in an energy storage system (for example, one or more batteries) for use in well site operations (for example, drilling hydraulic fracturing, logging, and other operations). In some aspects, batteries charged by or within the system 100 can be transported to one or more well sites to provide electrical power. The system 100 and associated methods can produce and use clean energy and support sustainability.

In the illustrated example implementation of FIG. 1, the system 100 includes a power charging sub-system 102 and a well site 120. Although each of power charging sub-system 102 and well site 120 are shown as singular components of the system 100, there can be multiple power charging sub-systems 102 and multiple well sites 120 in alternative implementations.

In some aspects, power charging sub-system 102 can be constructed at an oil and gas processing plant, such as where acid gasses are recycled from the plant operations and processing of hydrocarbons. In some aspects, the power charging sub-system 102 can be built on selected remote well sites where hydrocarbon is received from a well directly. Energy can be used for near-site (plant or well) operations (near the power charging sub-system 102) or it can be stored (as described herein) and transported from the site of the sub-system 102 to other remote operations (for example, at or near the multiple well sites 120).

Turning first to the power charging sub-system 102, the sub-system 102 includes, in this example, a gas separation plant 104, an acid gas separator 106, and a hydrogen engine 108. Each of the aforementioned components can be collocated (for example, placed on the same property and controlled by a single entity) or remotely located (for example, located on different properties and/or controlled by different entities). In this example, the gas separation plant 104 can receive hydrocarbon fluid 101 (for example, a hydrocarbon gas or mixed phase hydrocarbon fluid) from one or more wells 130. In some aspects, the hydrocarbon fluid 101 can be natural gas or methane (for example, if methane was separated from natural gas). Each of the wells 130 can be located on a terranean surface or body of water.

The gas separation plant 104 receives the hydrocarbon fluid 101 from the one or more wells 130 and operates to further process or separate one or more acid gasses 103 from the hydrocarbon fluid 101. In example implementations of system 100, the gas separation plant 104 can use a membrane (singular or multiple) system to separate the one or more acid gasses 103 from the hydrocarbon fluid 101. In some specific aspects, the separated acid gas 103 is hydrogen sulfide. But other acid gasses, such as hydrogen chloride or hydrogen fluoride are also contemplated by the present disclosure.

The separated acid gas or gasses 103, such as hydrogen sulfide 103, can be routed or provided to the acid gas separator 106. In example implementations, the acid gas separator 106 operates to separate hydrogen 105 from the hydrogen sulfide 103 through one or more sub-processes. For example, the acid gas separator 106 can utilize a Claus reaction, an electrolytic reaction, a thermal decomposition reaction, a biological reaction, or a combination thereof, to separate hydrogen 105 from the hydrogen sulfide 103.

In some aspects, the acid gas separator 106 uses the Claus reaction to produce hydrogen 105 and elemental sulfur by partially oxidizing gaseous hydrogen sulfide into water and sulfur in a two-step reaction that includes:

$$H_2S+3/2O_2 \rightarrow H_2O+SO_2$$

$$SO_2+2H_2S \rightarrow 3S+2H_2O.$$

The water produced in the second step is then used to produce hydrogen 105 by an electrolysis process:

$$H_2O \rightarrow H_2+\frac{1}{2}O_2.$$

In some aspects, the acid gas separator 106 uses an electrolytic reaction to produce hydrogen 105 and sulfur as a byproduct. For example, hydrogen sulfide 103 can be introduced to an electrolysis cell with an electrolyte at ambient or high temperatures to directly yield sulfur and hydrogen instead of sulfur and water (as in the Claus reaction). The gas molecules can be dissociated by a chemical oxidation reaction. The hydrogen molecules are accumulated at cathodic current and the sulfur molecules are accumulated at anodic current. For the chemical reaction, two electrons are required to produce ⅛ mole of S4 and 2 moles of $H_2$ according to:

$$H_2S+2H^+ \rightarrow 2e^- + \frac{1}{8}S_{4(anode)}$$

$$2H^+ + 2e^- \rightarrow H_{2(cathode)}.$$

In some aspects, the acid gas separator 106 uses a thermal decomposition reaction to produce hydrogen 105 and sulfur. For example, hydrogen sulfide 103 is heated up by the use of an external heat source at (for example, at 1000° C.) until the hydrogen sulfide 103 is dissociated into hydrogen 105 and oxygen. The reaction establishes thermodynamic equilibrium between the dissociation reaction and the recombination reaction:

$$H_2S \rightarrow H_2+\frac{1}{2}S.$$

In some aspects, the thermal decomposition reaction can include a catalyst. For example, hydrogen sulfide thermal separation into hydrogen and sulfur can be enhanced by using highly active heterogeneous catalysts at relatively low temperatures. Metal catalysts can be used to oxidize hydrogen sulfide at high temperature to minimize the sulfur dioxide formation at relatively low contact times:

$$H_2S \rightarrow H_2 + 3S.$$

Another form of a thermal decomposition reaction that can be used by the acid gas separator 106 to separate the hydrogen 105 from the hydrogen sulfide 103 can be a plasma or microwave irradiation thermal reaction. For example, plasma/microwave irradiation can be used to selectively excite the hydrogen sulfide molecule to initiate the decomposition by controlling a level of input energy required to initiate the decomposition. The reaction can target HSx species from an initially excited hydrogen sulfide molecule. This reaction can use low operating pressures and/or low hydrogen sulfide concentrations to maintain a stable plasma flow. Increasing a speed of conversion levels can also decrease $H_2S/H_2$ separation and cost.

In some aspects, the acid gas separator 106 uses a biological reaction to produce hydrogen 105 and sulfur. For example, hydrogen sulfide can be removed by the use of certain microorganisms that have an ability to harness energy from the hydrogen sulfide 103 and use it for their biological process to produce hydrogen 105. For instance, sulfide oxidizing bacteria (SOB) or chemotrophs can be used for hydrogen sulfide removal via oxidation, such bacterial species use hydrogen sulfide as an energy source in their chemosynthesis process. SOBs include several genera and the most common hydrogen sulfide-oxidizing bacteria are acidophilic, from the *Thiobacillus* genus. This chemotrophic thiobacteria can be used both aerobically and anaerobically. They grow and produce cell products by using inorganic carbon in carbon dioxide and use chemical energy from the oxidation of reduced inorganic compounds hydrogen sulfide.

In some aspects, the biological reaction includes aerobic removal of hydrogen sulfide using microbial processes. For example, under oxygen-limiting conditions, oxygen acts as an electron acceptor, hydrogen sulfide acts as an electron donor, and elemental sulfur is produced and can be recovered:

$$H_2S + 0.5O_2 \rightarrow S^0 + H_2O.$$

Under excess oxygen conditions, sulfate is produced, which leads to acidification:

$$H_2S + 2O_2 \rightarrow SO_4^{2-} + 2H^+.$$

In some aspects, the biological reaction includes anaerobic removal of hydrogen sulfide using microbial processes. For example, photosynthetic bacteria (phototrophs) can be used to bio-degrade hydrogen sulfide. This biological sulfide removal process offers the following advantages: only light is required and no need of oxygen. The overall photochemical reaction by which phototrophs oxidizes hydrogen sulfide to $S^0$ while reducing $CO_2$ to carbohydrates is:

$$2nH_2S + nCO_2 + \text{Light energy} \rightarrow 2nS^0 + n(CH_2O) + nH_2O.$$

The biological reaction can take place inside a bioreactor. The bioreactor, in some aspects, can be a biofilter reactor. In some aspects, the bioreactor can be a bioscrubber reactor. The bioscrubber can include two phases: first absorption of hydrogen sulfide by a liquid followed by microbe mediated oxidation of hydrogen sulfide (for example, a commercially available bioscrubber is Thiopaq). This technology uses chemotrophic bacteria that oxidize hydrogen sulfide to solid elemental sulfur. Unlike other liquid processes, bacteria produce enzymes that covers the sulfur particles converting them to hydrophilic non-sticky particles, hydrophobic sulfur. Because sulfur particles are present throughout the process wherever the liquid solution exists, it follows that non-sticky sulfur particles lead to significantly less downtime for plant maintenance.

A biofilter reactor involves three phases (gas, liquid, solid), and is made with immobilized microbes that are imbedded in a filter bed and act as a biofilm. The biofiltration of hydrogen sulfide involves the following: (i) hydrogen sulfide transfer from gaseous phase to liquid phase, (ii) the diffusion of hydrogen sulfide to the biofilm, (iii) hydrogen sulfide adsorption the biofilm, and (iv) oxidation of hydrogen sulfide by microbes forming the biofilm.

Regardless of the reaction or reactions employed by the acid gas separator 106, hydrogen 105 is separated from the acid gas 103 (for example, hydrogen sulfide 103) and provided to the hydrogen engine 108. Additional, a stream of sulfur 119 is output from the acid gas separator 106 for further processing. For example, the sulfur 119 can be used for several applications such as for cement, detergents, and/or pesticides industries. Sulfur dioxide also can be used to generate electricity. Sulfur dioxide can reacted with calcite ($CaCO_3$) to produce anhydrite ($CaSO_4$) in an outlet gas desulfurization unit. The desulfurization reaction produces "exothermic" heat that can be converted to electricity (that can be used to charge power storage units 110 or as electrical power 111) by passing the exhaust gas through a heat recovery steam generator. In some aspects, therefore, the power generator system 100 also includes generating power through the use of the sulfur 119 to boost overall system efficiency.

The hydrogen engine 108 is operated to produce electrical power 109 (or electrical power 111, or both) from the hydrogen 105. The generated hydrogen 105 from the example reaction processes can be used to power the well site 120 or store energy for future usage.

Figure 2:
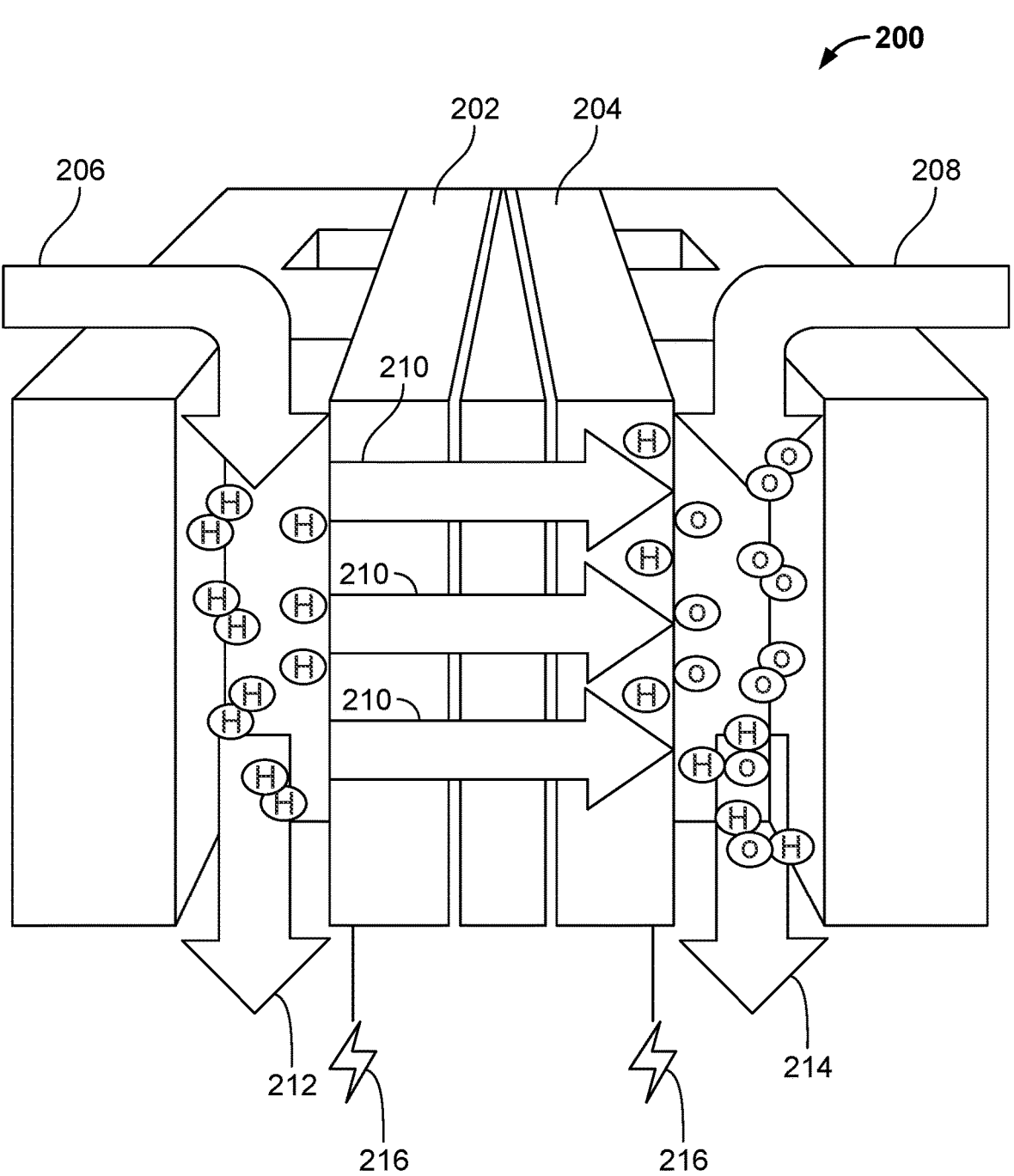
FIG. 2 is a schematic illustration of a hydrogen fuel cell of a hydrogen engine of a power generation system according to the present disclosure.

For instance, the hydrogen 105 can be converted to electricity by reverse electrolytic method, such as by fuel cells. In some aspects, the hydrogen engine 108 includes one or more hydrogen fuel cells, such as a hydrogen fuel cell 200 shown in FIG. 2. As shown in FIG. 2, the hydrogen fuel cell 200 includes an anode 202 and a cathode 204 that are positioned to receive hydrogen gas 206 (in other words, the hydrogen 105) and oxygen 208 (such as from ambient air). In the fuel cell 200, the hydrogen gas 206 is converted in to positively charged hydrogen ions and negatively charged hydrogen ions (protons and electrons). The anode 202 receives the hydrogen gas 206 and the cathode 204 collects oxygen 208 from air. Protons will pass through a membrane from the anode 202 to the cathode 204. This will create a flow of direct current electricity 216 between terminals of the anode 202 and cathode 204, onto which a power storage unit (for example, a rechargeable unit such as a rechargeable battery) can be connected to receive and store the direct current electricity 216. As shown in FIG. 2, the migrated positive ions combine with the oxygen 208 to produce water 214 as a waste output, while excess hydrogen 212 is also produced. In some cases, one fuel cell can produce 0.6-0.8 V under load. The hydrogen engine 108 can include or combine multiple fuel cells 200 to obtain higher voltage to charge multiple power storage units.

Turning back to FIG. 1, the power storage units 110 (for example, rechargeable batteries) are connected to the hydrogen engine 108 to receive electrical power 109. Once charged (for example, fully), the power storage units 110 can be transported 113 to the well site 120 as shown. In addition or alternatively, electrical power 111 from the hydrogen engine 108 can be routed directly to a power control system 112 at the well site 120 that manages electrical power use at the well site 120. In some aspects, the electrical power 111, or charged power storage units 110, can also be used to power one or more of the gas separation plant 104, the acid gas separator 106, or the hydrogen engine 108.

In some aspects, well site 120 includes operations that are remote in the sense, for example, that such operations are not or cannot be powered by an electrical grid or public utility. Thus, electrical power for such operations can be provided by the charged power storage units 110.

In some aspects, the power storage units 110 can be one or more of lead-acid, nickel cadmium (NiCd), Lithium-ion, Lithium-ion polymer, alkaline batteries, or a combination thereof. For instance, as a Lithium-ion polymer battery, the power storage unit 110 can be composed of several identical secondary ells in parallel which can help to increase the discharge-current capability. A Lithium-ion polymer battery is available on series for a higher voltage requests and are not required to be held in an organic solvent. Therefore, a Lithium-ion polymer battery can be easier to transport compared to Lithium-ion batteries. The battery design cost also can be lower and has a wide range of packaging shapes and reliability.

The power storage units 110 can also be all iron flow batteries (redox flow batteries). Redox flow batteries are based on all iron flow, which can be used for electrical energy storage. Their capacity is 10 KWh-800 MWh and have 15000-20000 days of life time which is suitable for the system 100.

At the well site 120, one or more well site operation components can receive electrical power 117 through the electrical power control system 122, which originates as electrical power 115 from the power storage units 110 transported to the well site 120 or the electrical power 111 (or both). In some aspects, the electrical power control system 122 can include circuits, transformers, inverters, rectifiers, circuit breakers, fuses, and/or any other power transmission components, as well as a microprocessor-based controller to control operation of such components, when needed, according to the power requirements of any one or more of the well site components 124a-124e. In this example, the well site 120 includes one or more of logging equipment 124a, pumps (for example, a frac spread, an electrical submersible pump, a sub-surface fluid pump) 124b, blenders 124c, wireline equipment 124d, and/or sand systems 124e. Each of the aforementioned components, while conventionally operated on power supplied by diesel engines, can be powered by the power storage units 110 at the well site 120 (and/or electrical power 111).

In some aspects, the electrical power control system 122 optimizes the energy utilization based of the electrical power 115 and/or 111 using a smart microgrid system. The system 122 can utilize or implement different algorithms to route the electrical power 115 and/or 111 to the well site components 124a-124e based on, for example, an availability of resources, such as by alternating between the generated power on-site and storing/withdrawing power 115 from the power storage units 110.

FIG. 3 is a flowchart that describes an example method 300 of generating electrical power according to the present disclosure. In some aspects, method 300 can be performed with or by the power generation system 100. Method 300 can begin at step 302, which includes producing hydrocarbons including natural gas from one or more wells. For example, in some aspects, a well or multiple wells will produce hydrocarbon fluids, such as oil and natural gas. The natural gas can also include constituent components such as methane and other components. One or more of the constituent components can be acid gasses, such as carbon dioxide, hydrogen sulfide, and other gasses.

Method 300 can continue at step 304, which includes separating the natural gas from the produced hydrocarbons. For example, oil and natural gas are often produced in a mixed phase hydrocarbon fluid. The natural gas can be separated from the oil and further processed as described herein.

Method 300 can continue at step 306, which includes processing the natural gas to produce at least one acid gas. For example, the separated natural gas can still include constituent hydrocarbon gasses as well as acid gasses, such as hydrogen sulfide and other gasses. Generally, acid gasses must be removed from natural gas for its use as a hydrocarbon fuel. The removed acid gasses are often harmful and must be disposed of; but according the present disclosure, such acid gasses can be used to generate electrical power.

Method 300 can continue at step 308, which includes processing the acid gas into hydrogen and at least one byproduct. For example, as previously described, an acid has separator can use one or more separation reactions (for example, Claus reaction, electrolytic reaction, thermal decomposition reaction, biological reaction) to separate hydrogen from the acid gas (such as hydrogen sulfide). In some aspects, the byproduct can be sulfur.

Method 300 can continue at step 310, which includes generating electrical power from a hydrogen engine with the hydrogen. For example, as previously described, a hydrogen engine can include or consist of one or more hydrogen fuel cells that generate electrical power with hydrogen and oxygen (for example, ambient air) in an electrolysis reaction that also produces excess hydrogen and water.

Method 300 can continue at step 312, which includes charging at least one rechargeable power unit with the generated electrical power. For example, one or more rechargeable power units, such as rechargeable batteries, can be electrically connected to the hydrogen engine to charge, thereby storing the electrical power generated by the hydrogen engine.

Method 300 can continue at step 314, which includes delivering the charged at least one rechargeable power unit to a well site. For example, in some aspects, once one or more batteries have been charged by the hydrogen engine, they can be taken to one or more well sites for use. In some aspects, step 314 can also include keeping some of the one or more charged batteries at the hydrogen engine or acid gas separator (or both) or at another location separate from the well site.

Method 300 can continue at step 316 (which can follow from either step 312 or 314 or both, in series or in parallel), which includes operating at least one electrically-operated machine at a well site with the generated electrical power (directly or through an electric power control system). For example, charged batteries can operate a number of well site components, such as pumps, blenders, logging equipment, and other equipment that requires or can use electrical power. In some aspects, such electrical power can be delivered directly from step 312 by electrically connecting the hydrogen engine to the electrically-operated machine(s) (directly or through, for instance, a microgrid of an electric power control system).

Figure 4:
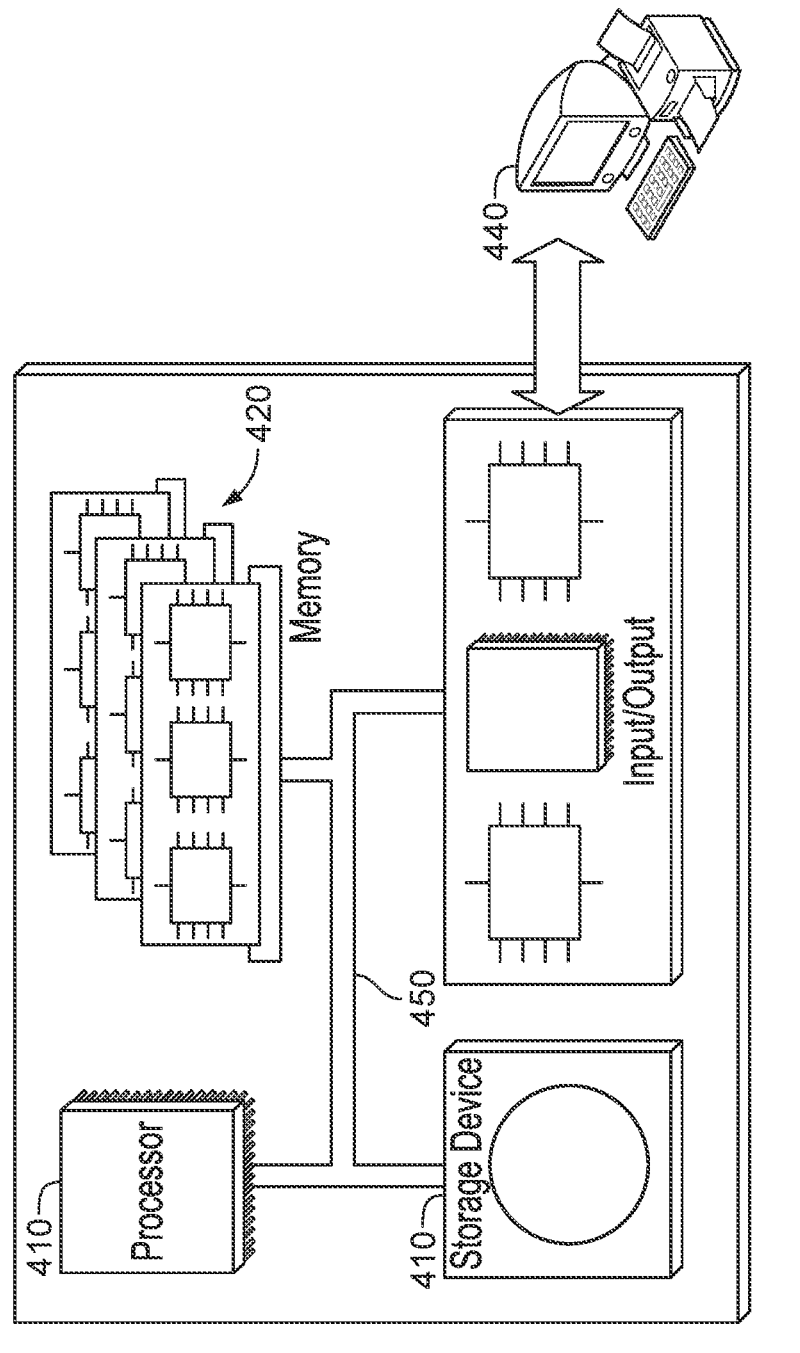
FIG. 4 shows a schematic drawing of an electrical power control system that can be used in the example system of FIG. 1 according to the present disclosure.

FIG. 4 shows a schematic drawing of an electrical power control system that can be used in the example system of FIG. 1 according to the present disclosure. For example, all or parts of the control system (or controller) 400 can be used for the operations described previously, for example as or as part of the electrical power control system 122 shown in FIG. 1. The controller 400 is intended to include various forms of digital computers, such as printed circuit boards (PCB), processors, digital circuitry, or otherwise. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 400 includes a processor 410, a memory 420, a storage device 430, and an input/output device 440. Each of the components 410, 420, 430, and 440 are interconnected using a system bus 450. The processor 410 is capable of processing instructions for execution within the controller 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the control system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the controller 400. In one implementation, the storage device 430 is a computer-readable medium. In various different implementations, the storage device 430 may be a floppy disk device, a hard disk device, an optical disk device, a tape device, flash memory, a solid state device (SSD), or a combination thereof.

The input/output device 440 provides input/output operations for the controller 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, solid state drives (SSDs), and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) or LED (light-emitting diode) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method of generating electric power for well site operations, comprising:

processing a hydrocarbon fluid produced from a subterranean formation, through a wellbore, and to a terranean surface into at least one acid gas;

processing the at least one acid gas into hydrogen;

generating, with the hydrogen, electrical power from a hydrogen engine;

providing a first portion of the generated electrical power to power at least one electrically-operated machine to perform at least one well site operation at a well site that is remote from and electrically decoupled from an electrical grid or public utility; and simultaneously with providing the generated electrical power to power at least one electrically-operated machine to perform the at least one well site operation at the well site, providing a second portion of the generated electrical power to charge at least one rechargeable battery.

2. The method of claim 1, wherein the at least one acid gas comprises hydrogen sulfide, and processing the at least one acid gas into the hydrogen comprises converting the hydrogen sulfide into the hydrogen through a Claus reaction, comprising:

processing the hydrogen sulfide and oxygen into water and sulfur dioxide;

processing the sulfur dioxide and the hydrogen sulfide into sulfur and water; and processing the water into the hydrogen and oxygen.

3. The method of claim 1, wherein the at least one acid gas comprises hydrogen sulfide, and processing the at least one acid gas into the hydrogen comprises converting the hydrogen sulfide into the hydrogen through an electrolytic reaction, comprising:

processing the hydrogen sulfide and at least two electrons to produce sulfur at an anode of an electrolysis cell of the electrolytic reaction and the hydrogen at a cathode of the electrolysis cell.

4. The method of claim 1, wherein the at least one acid gas comprises hydrogen sulfide, and processing the at least one acid gas into the hydrogen comprises converting the hydrogen sulfide into the hydrogen through a thermal decomposition reaction, comprising:

dissociating, with heat from an external heat source or a microwave source, the hydrogen sulfide into the hydrogen and sulfur.

5. The method of claim 4, further comprising enhancing the dissociation with a catalyst.

6. The method of claim 1, wherein the at least one acid gas comprises hydrogen sulfide, and processing the at least one acid gas into the hydrogen comprises converting the hydrogen sulfide into the hydrogen through a biological reaction, comprising:

introducing one or more microorganisms to the hydrogen sulfide; and producing the hydrogen and sulfur from the hydrogen sulfide through one or more biological processes performed with the one or more microorganisms.

7. The method of claim 1, wherein generating, with the hydrogen, electrical power from the hydrogen engine comprises:

introducing the hydrogen and atmospheric air into at least one fuel cell of the hydrogen engine;

converting the hydrogen into positively and negatively charged hydrogen ions in the at least one fuel cell;

flowing the positively charged hydrogen ions from an anode of the at least one fuel cell to a cathode of the at least one fuel cell to generate an electrical current to produce the electrical power; and producing water from the at least one fuel cell by combining the negatively charged hydrogen ions with the atmospheric air.

8. The method of claim 7, wherein providing the second portion of the generated electrical power to charge at least one rechargeable battery comprises:

electrically connecting the at least one rechargeable battery to the at least one fuel cell; and electrically charging the at least one rechargeable battery with the produced electrical power from the at least one fuel cell.

9. The method of claim 8, further comprising, subsequent to electrically charging the at least one rechargeable battery with the produced electrical power from the at least one fuel cell:

delivering the charged at least one rechargeable battery to the well site;

electrically connecting the charged at least one rechargeable battery to an electrically-operated machine at the well site; and operating the electrically-operated machine at the well site to perform the well site operation with the charged at least one rechargeable battery.

10. The method of claim 7, wherein providing the first portion of the generated electrical power to power the at least one electrically-operated machine to perform the at least one well site operation at the well site comprises:

directly connecting the at least one fuel cell to the at least one electrically-operated machine at the well site; and operating the electrically-operated machine at the well site to perform the well site operation with the produced electrical power.

11. The method of claim 10, wherein the electrically-operated machine comprises at least one of a hydraulic fracturing pump, a hydraulic fracturing blender, a logging machine, a wireline machine, an electrical submersible pump, a sub-surface fluid pump, or a sand system.

12. An electric power generation system for well site operations, comprising:

a hydrocarbon processing sub-assembly configured to process a hydrocarbon fluid produced from a subterranean formation, through a wellbore, and to a terranean surface into at least one acid gas;

an acid gas processing sub-assembly configured to receive the at least one acid gas from the hydrocarbon processing sub-assembly and process the at least one acid gas into hydrogen;

at least one hydrogen engine configured to generate electrical power from the hydrogen processed by the acid gas processing sub-assembly to power at least one electrically-operated machine with a first portion of the generated electrical power to perform at least one well site operation at a well site that is remote from and electrically decoupled from an electrical grid or public utility; and at least one power storage unit configured to electrically couple to the at least one hydrogen engine to receive and store a second portion of the generated electrical power simultaneously with powering the at least one electrically-operated machine with the first portion of the generated electrical power for delivery to the well site.

13. The electric power generation system of claim 12, wherein the at least one acid gas comprises hydrogen sulfide, and the acid gas processing sub-assembly is configured to convert the hydrogen sulfide into the hydrogen through a Claus reaction by performing operations comprising:

processing the hydrogen sulfide and oxygen into water and sulfur dioxide;

processing the sulfur dioxide and the hydrogen sulfide into sulfur and water; and processing the water into the hydrogen and oxygen.

14. The electric power generation system of claim 12, wherein the at least one acid gas comprises hydrogen sulfide, and the acid gas processing sub-assembly is configured to convert the hydrogen sulfide into the hydrogen through an electrolytic reaction by performing operations comprising:

processing the hydrogen sulfide and at least two electrons to produce sulfur at an anode of an electrolysis cell of the electrolytic reaction and the hydrogen at a cathode of the electrolysis cell.

15. The electric power generation system of claim 12, wherein the at least one acid gas comprises hydrogen sulfide, and the acid gas processing sub-assembly is configured to convert the hydrogen sulfide into the hydrogen through a thermal decomposition reaction by performing operations comprising:

dissociating, with heat from an external heat source or a microwave source, the hydrogen sulfide into the hydrogen and sulfur.

16. The electric power generation system of claim 15, wherein the acid gas processing sub-assembly is configured to convert the hydrogen sulfide into the hydrogen through the thermal decomposition reaction by enhancing the dissociation with a catalyst.

17. The electric power generation system of claim 12, wherein the at least one acid gas comprises hydrogen sulfide, and the acid gas processing sub-assembly is configured to convert the hydrogen sulfide into the hydrogen through a biological reaction by performing operations comprising:

introducing one or more microorganisms to the hydrogen sulfide; and producing the hydrogen and sulfur from the hydrogen sulfide through one or more biological processes performed with the one or more microorganisms.

18. The electric power generation system of claim 12, wherein the at least one hydrogen engine comprises at least one fuel cell, and the at least one hydrogen engine is configured to generate electrical power from the hydrogen processed by the acid gas processing sub-assembly by performing operations comprising:

introducing the hydrogen and atmospheric air into the at least one fuel cell;

converting the hydrogen into positively and negatively charged hydrogen ions in the at least one fuel cell;

flowing the positively charged hydrogen ions from an anode of the at least one fuel cell to a cathode of the at least one fuel cell to generate an electrical current to produce the electrical power; and producing water from the at least one fuel cell by combining the negatively charged hydrogen ions with the atmospheric air.

19. The electric power generation system of claim 18, wherein the at least one power storage unit comprises at least one rechargeable battery electrically connected to the at least one fuel cell, and the at least one fuel cell is configured to electrically charge the at least one rechargeable battery with the produced electrical power from the at least one fuel cell.

20. The electric power generation system of claim 19, wherein the at least one rechargeable battery is configured to electrically connect to the electrically-operated machine at the well site to operate the electrically-operated machine at the well site to perform a well site operation with the charged at least one rechargeable battery.

21. The electric power generation system of claim 18, wherein the at least one fuel cell is configured to electrically connect to the electrically-operated machine at the well site to operate the electrically-operated machine at the well site to perform the well site operation with the produced electrical power.

22. The electric power generation system of claim 21, wherein the electrically-operated machine comprises at least one of a hydraulic fracturing pump, a hydraulic fracturing blender, a logging machine, a wireline machine, an electrical submersible pump, a sub-surface fluid pump, or a sand system.

23. An electric power generation system for well site operations, comprising:

a hydrocarbon processing sub-assembly configured to process a hydrocarbon fluid produced from a subterranean formation, through a wellbore, and to a terranean surface into hydrogen sulfide;

means for processing the hydrogen sulfide into hydrogen;

at least one hydrogen fuel cell configured to generate electrical power from the hydrogen;

at least one rechargeable battery configured to electrically couple to the at least one hydrogen fuel cell to receive and store a first portion of the generated electrical power for delivery to a well site that is remote from and electrically decoupled from an electrical grid or public utility; and at least one electrically-operated machine operable with a second portion of the generated electrical power to perform at least one well site operation at the well site simultaneously with delivery of the at least one rechargeable battery to the well site.

24. The electric power generation system of claim 23, wherein the means for processing comprises at least one of:

means for processing the hydrogen sulfide into hydrogen through a Claus reaction;

means for processing the hydrogen sulfide into hydrogen through a thermal decomposition reaction;

means for processing the hydrogen sulfide into hydrogen through a biological reaction; or means for processing the hydrogen sulfide into hydrogen through an electrolytic reaction.

25. The electric power generation system of claim 23, wherein the means for processing the hydrogen sulfide into hydrogen comprises means for processing the hydrogen sulfide into sulfur.

26. The electric power generation system of claim 25, wherein the sulfur is usable to generate additional electrical power with an outlet gas desulfurization unit through a desulfurization reaction.

\*  \*  \*  \*  \*